United States Patent
Pedrazzini

(10) Patent No.: US 8,863,802 B2
(45) Date of Patent: Oct. 21, 2014

(54) APPARATUS FOR AUTOMATIC MARKING OF CONTAINERS OF BIOLOGICAL SAMPLES

(75) Inventor: Gianandrea Pedrazzini, Paradiso (CH)

(73) Assignee: Inpeco Holding Ltd., Valletta (MT)

( * ) Notice: Subject to any disclaimer, the term of this patent is extended or adjusted under 35 U.S.C. 154(b) by 206 days.

(21) Appl. No.: 13/003,243

(22) PCT Filed: Jul. 2, 2009

(86) PCT No.: PCT/EP2009/058360
§ 371 (c)(1),
(2), (4) Date: Jan. 7, 2011

(87) PCT Pub. No.: WO2010/003880
PCT Pub. Date: Jan. 14, 2010

(65) Prior Publication Data
US 2011/0114263 A1   May 19, 2011

(30) Foreign Application Priority Data

Jul. 10, 2008 (IT) .......................... MI2008A001258

(51) Int. Cl.
*G01N 35/00* (2006.01)
(52) U.S. Cl.
CPC .................. *G01N 35/00732* (2013.01); *G01N 2035/00861* (2013.01)
USPC ........... 156/361; 156/378; 156/379; 156/387; 422/63; 422/65; 422/67

(58) Field of Classification Search
USPC ........ 156/361, 378, 379, 387; 422/63, 65, 67, 422/562; 209/529, 530
See application file for complete search history.

(56) References Cited

U.S. PATENT DOCUMENTS

| | | | | |
|---|---|---|---|---|
| 5,688,361 A | * | 11/1997 | Itoh ............................... | 156/362 |
| 5,893,263 A | * | 4/1999 | Matsumoto et al. .......... | 156/387 |
| 6,138,868 A | * | 10/2000 | Yuyama et al. ............ | 221/312 R |
| 2003/0066841 A1 | | 4/2003 | Hebron et al. | |
| 2007/0134131 A1 | | 6/2007 | Watson et al. | |

FOREIGN PATENT DOCUMENTS

| | | |
|---|---|---|
| EP | 0 819 470 A1 | 1/1998 |
| JP | 2001-264339 A | 9/2001 |

* cited by examiner

*Primary Examiner* — George Koch
(74) *Attorney, Agent, or Firm* — Birch, Stewart, Kolasch & Birch, LLP

(57) ABSTRACT

An apparatus for automatically marking laboratory test tubes in the stage of drawing biological material to be analyzed, which includes two or more distributors of test tubes of different types that are selectable by a control unit and are suitable for feeding test tubes to a test-tubes positioning device which in turn is suitable for presenting correctly positioned test tubes to a computerized labelling machine containing a printer for printing barcodes on labels. Each distributor includes an automatic drawing and discharging device for drawing and discharging single test tubes from a container of test tubes of a selected distributor to the positioning device.

2 Claims, 6 Drawing Sheets

APPARATUS FOR AUTOMATIC MARKING OF CONTAINERS OF BIOLOGICAL SAMPLES

This application is a national stage entry of PCT/EP09/58360, filed on Jul. 2, 2009.

The present invention relates to an apparatus for automatic marking of containers of biological samples.

The admittance of a patient to a health facility to make use of services entails, in almost all cases, identifying the patient and, if diagnostic examinations have to be conducted, the corresponding drawing of biological material to be analyzed (such as urine, blood, etc. contained in test tubes or other containers).

When managing diagnostic analyses of biological products drawn from patients it is very important and problematic to ensure an absolutely unequivocal correspondence between the patient and the biological material.

During drawing, the biological material is drawn and associated with the patient by using containers that are either previously identified and marked or are "anonymous" and marked at the moment of drawing.

Marking a container of biological material means applying a mark thereto, for example an adhesive label, containing all the information that is necessary for associating the biological material unequivocally with the original patient, possibly including further information that is suitable for identifying the type of biological material contained and the destination (to which laboratory it has to be sent and what tests have to be conducted).

More frequently, the applied label also comprises a barcode that is readable by suitable reading devices used as an unequivocal identification code and associating the biological material with the patient data.

The process disclosed above has some "inefficiencies" that are mainly caused by human errors of the operators having the task of marking the containers manually.

The consequences of these inefficiencies are:

risk of "mismatching". The greatest risk that an analysis laboratory may incur is an incorrect association of the patient with the drawn biological material and, at a later stage, of the patient with the report. In view of the high level of manual management of the process it can be understood how significant errors may arise that are due to so-called "mismatching" or mixing up of test tubes and/or analytical results (reports) belonging to different patients.

Slowness of the process. The process is slow and is sometimes easily subject to delays. Let the moment be considered in which the operator tasked with drawing has to affix the labels to the test tubes, checking that they are correctly associated with the tests to be conducted (which are distinguishable by the colour of the cap of the test tube).

In order to understand how easily and frequently the problems disclosed above can occur, it must be emphasized that a laboratory, even of medium size, receives each day several hundred (or thousands) of test tubes to examine; each of these test tubes containing the biological samples (mother test tubes) can in turn give rise to a certain number of test tubes (daughter test tubes) in which the biological material is distributed.

The object of the present invention is to make an apparatus for marking containers of biological material such as to overcome the problems illustrated above.

According to the invention, the object is achieved with an apparatus as disclosed in claim 1.

The labeling machine comprises a rolled belt supporting the labels to be printed and subsequently to be applied to the test tube by a system of rollers.

The apparatus that is the object of this invention consists of a variable number of distributors of test tubes that are suitable for presenting, on the basis of needs, test tubes of various dimensions and with differently coloured caps.

The need to use several distributors arises from the fact that on the basis of the biological material and the type of analyses to be conducted thereupon, the test tubes differ in size and cap colour. On the basis of the request, the test-tubes container is thus activated that contains the desired type of test tube (size and cap colour).

These and other features of the present invention will be made clearer from the following detailed description of an embodiment thereof illustrated by way of non-limiting example in the attached drawings, in which FIG. 1 shows a perspective view of the apparatus for marking test tubes of biological material;

Figure 1:
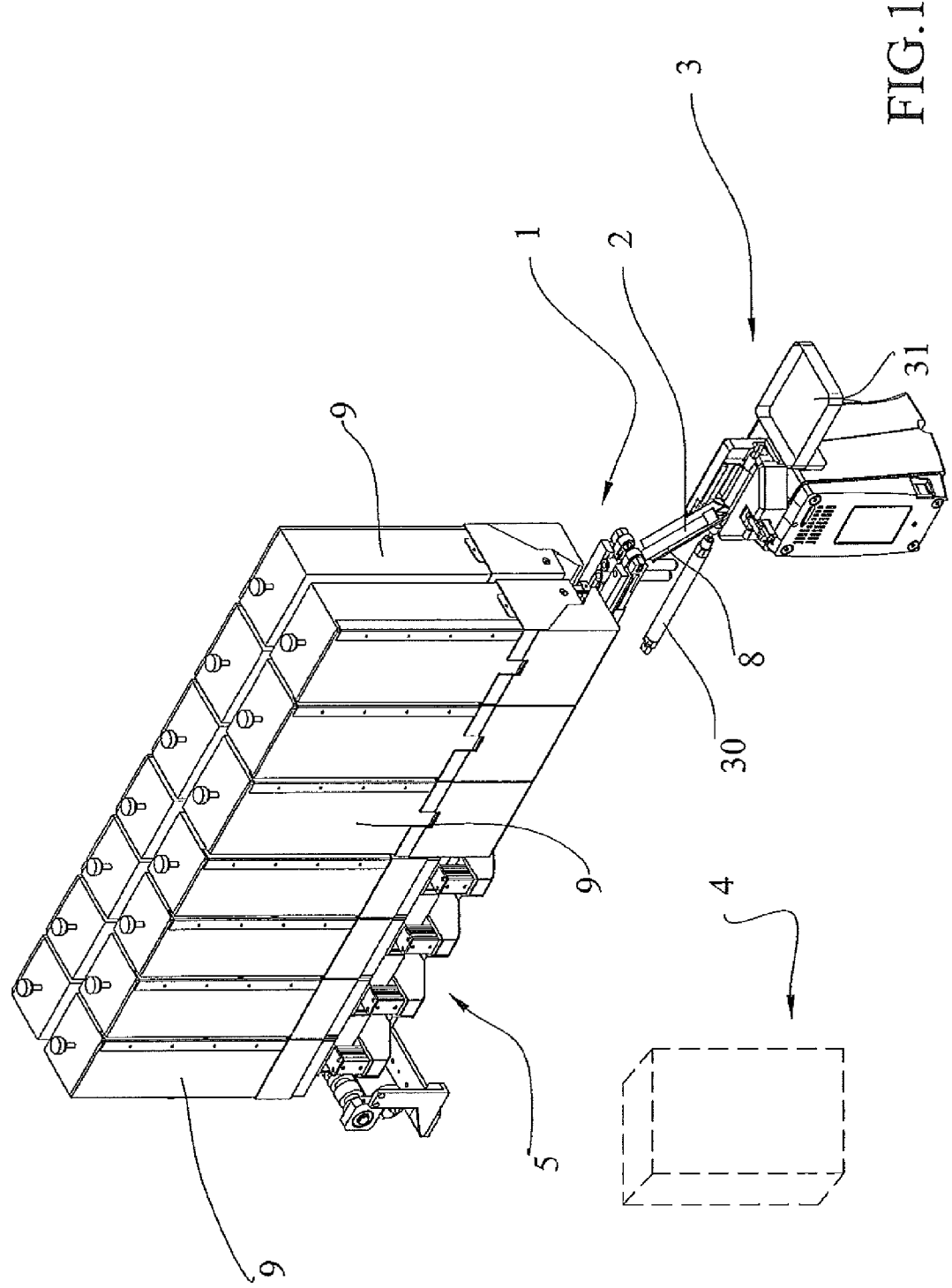

In FIG. 1 an apparatus according to the present invention is shown comprising a test-tube 2 positioning device 1 that is suitable for supplying an automatic marking device or a labeling machine 3.

Said devices are coordinated, during the various stages of the automatic marking process, by a control unit 4, represented, for example, by software installed in a personal computer, having above all the possibility of receiving and sending information from and to further external control units.

Figure 5:
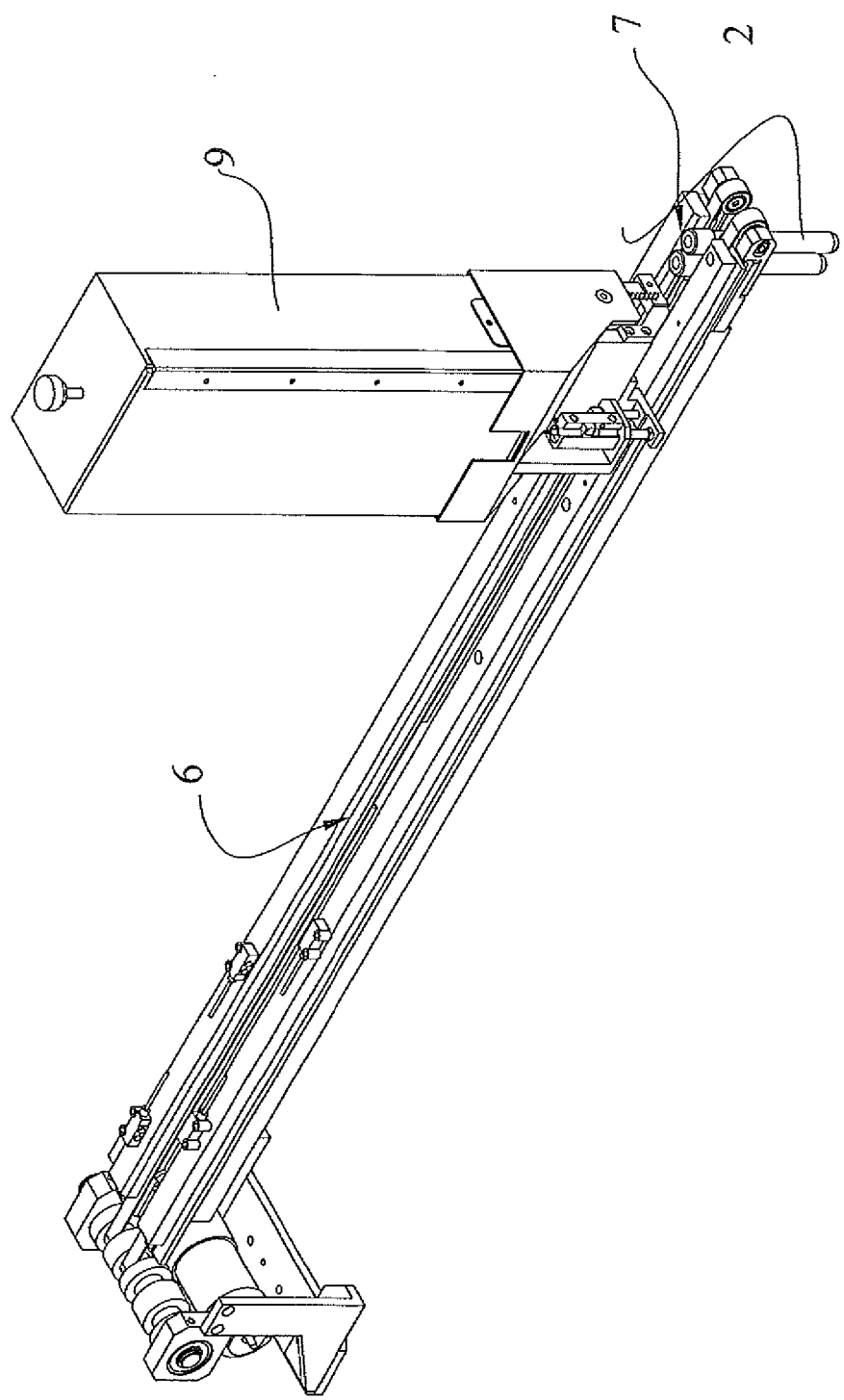
FIG. 5 shows a perspective view of the positioning device with the test-tube distributors having been removed except for one.

The positioning device 1, as disclosed in Italian patent application MI2008A00010, has the task of positioning test tubes 2 in a determined position, as shown in FIG. 5, corresponding to the vertical position with the cap facing upwards, such that the test tubes reach the labeling machine 3 in the preset position for a correct marking process.

The test tubes 2 are supplied to the positioning device 1 by distributors 5 (FIGS. 3 and 4), that are found in a variable number, preferably from 2 to 14, each arranged for dispensing test tubes having given features (on the basis of the size and colour of the cap). The disclosed embodiment comprises 14 distributors of test tubes 5 (FIG. 1).

The need to use test tubes of different sizes and which have caps of different colours arises from the fact that generally, in a hospital facility or in an analysis laboratory the biological samples and the analyses to be performed thereupon are differentiated by the size and colour of the cap of the test tube used as a container.

For example, a laboratory could establish that the test tubes containing blood on which clinical chemical analyses have to be conducted have to have a cap of a given colour and have a determined diameter or height.

Generally, the test tubes can have diameters of 13 mm or 16 mm and heights of 75 mm or 100 mm.

The disclosed embodiment is useful for processing test tubes of different heights having a diameter amounting to 13 mm but it should be specified that the apparatus that is the object of the present invention is adaptable to all types of commercially available test tubes by simply dimensioning the parts in a suitable manner.

Thus on the basis of the request coming from the laboratory the control unit 4 activates the distributor 5 containing the desired type of test tube.

Figure 4:
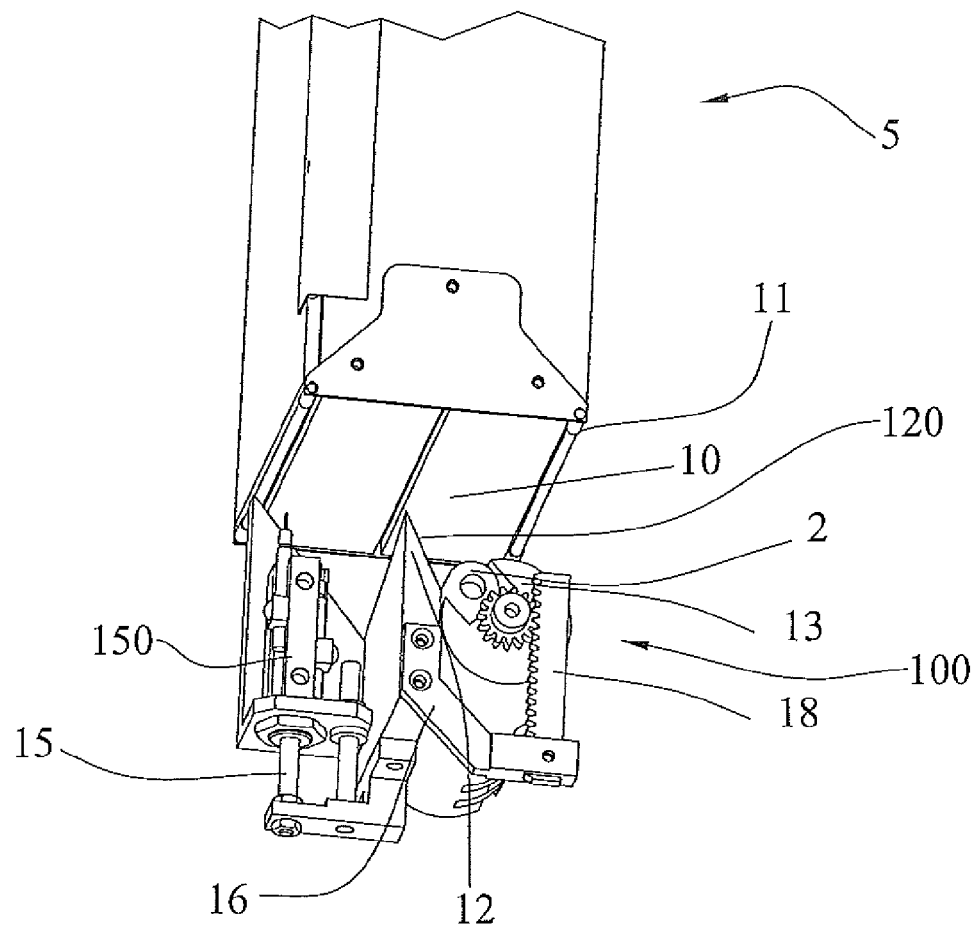
FIG. 4 shows a perspective bottom view of the configuration of FIG. 3, with the loading and discharging device in the test-tube loading position.

The distributor 5 comprises a container 9 of test tubes 2, having, as a lower base, two doors 10 balancing on pivots 11 (FIG. 4).

Figure 3:
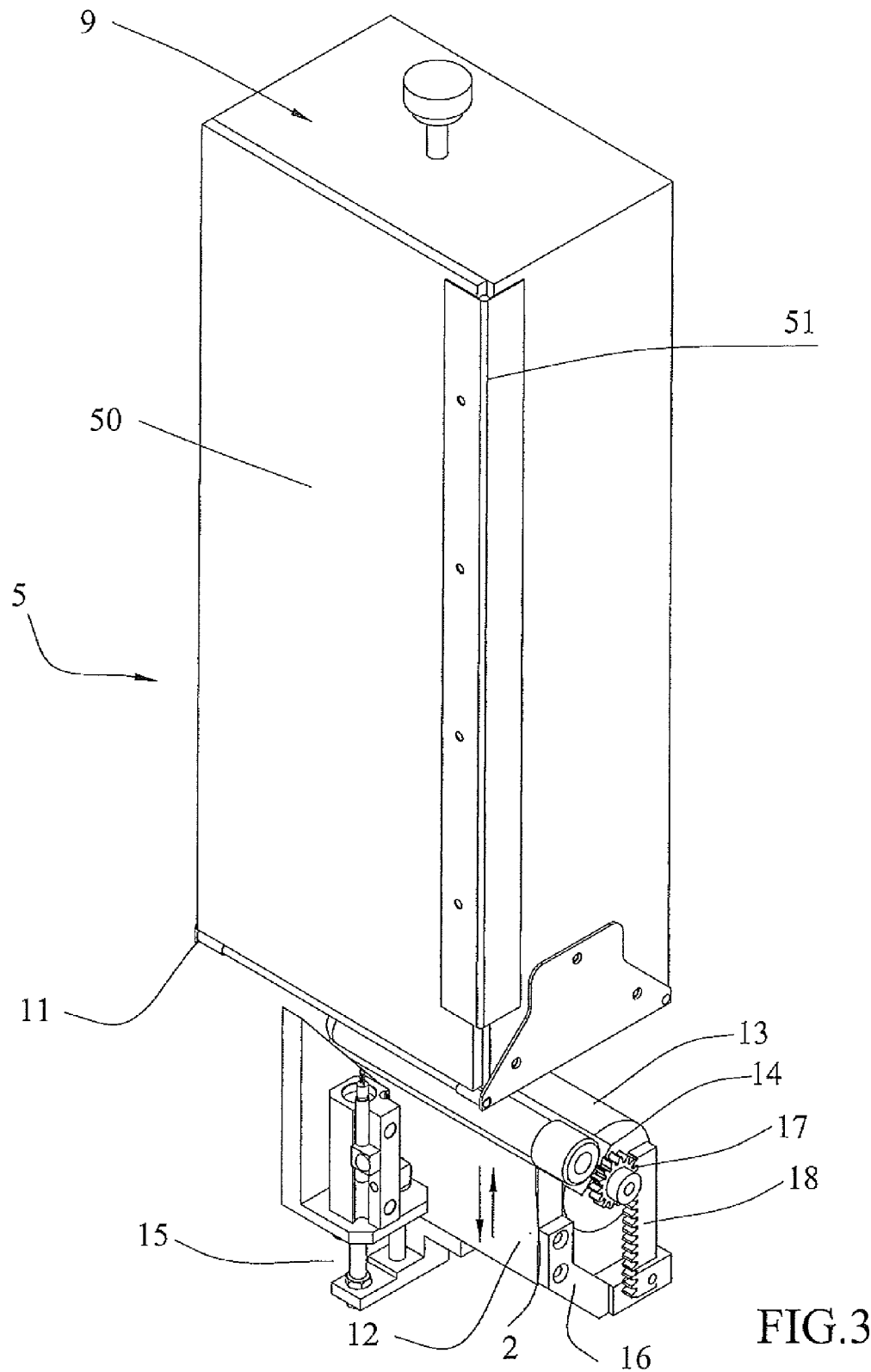
FIG. 3 shows a perspective view of a test-tube distributor.

The container 9 is removable and comprises a lateral door 50 that is openable owing to the presence of a hinge 51, in which the test tubes can be conveniently inserted into a separate seat (FIG. 3).

A wedge 12 (FIG. 4) comprised in a device 100 for drawing and discharging a single test tube from the container 9 to a positioning device 1, performing a vertical movement from bottom to top and vice versa by means of a piston 15 (as indicated in the arrows in FIG. 3), is introduced between the two doors 10, which are opened so as to let a single test tube pass, inside the container 9, producing a remixing of the test tubes inside the container and enabling the passage of one test tube at a time outside the container 9; the substantial disorder inside the container 9 means that simply opening the doors 10 is not statistically sufficient to let a single test tube pass as it is jammed between further test tubes inside the container 9; the wedge 9 substantially "unjams" the test tube that has to be discharged; weight force alone is not sufficient.

The unjammed test tube slides down the tilted side 120 of the wedge 12, passing through the two doors 10 to a housing 14 comprised in a rotor 13 of the device 100.

A rotation of the rotor 13 (as indicated by the arrow in FIG. 4A) enables the test tube 2 to be released that is present in the housing 14 on the positioning device 1.

This rotation occurs following the downward movement of the wedge 12, which is always generated by the piston 15 (FIGS. 3 and 4) leaving the fixed cylinder 150.

A support 16, which is integral with the wedge 12, moving in a vertical direction, generates the transfer in the same direction as a rack 18 on which a gear 17 is engaged, with consequent rotation of the rotor 13.

Figure 4A:
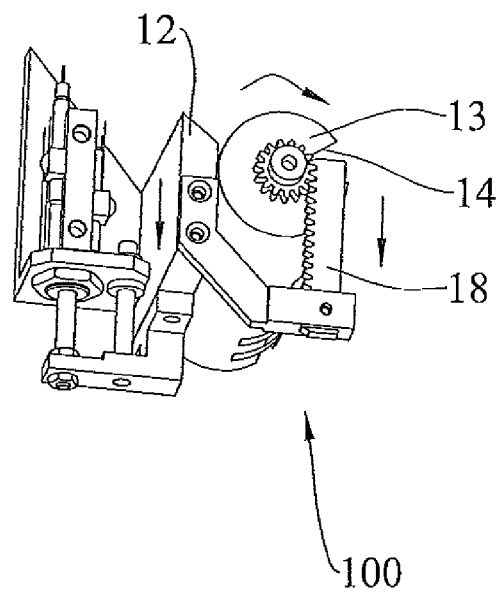
FIG. 4A shows a perspective bottom view of the loading and unloading device in the test-tube discharging position.

During the stage of loading the test tube the wedge 12 and the rack 18 are moved upwards, rotating the rotor 13 anti-clockwise (FIG. 4); during the stage of discharging the test tube the wedge 12 and the rack 18 are moved downwards to rotate the rotor 13 clockwise until it takes on the position in FIG. 4A.

A test tube, released by the distributor 5, reaches the positioning device 1, where it is "straightened" and conveyed by the conveyor belts 6 to a stroke-stop point 7 (FIG. 5).

Figure 2:
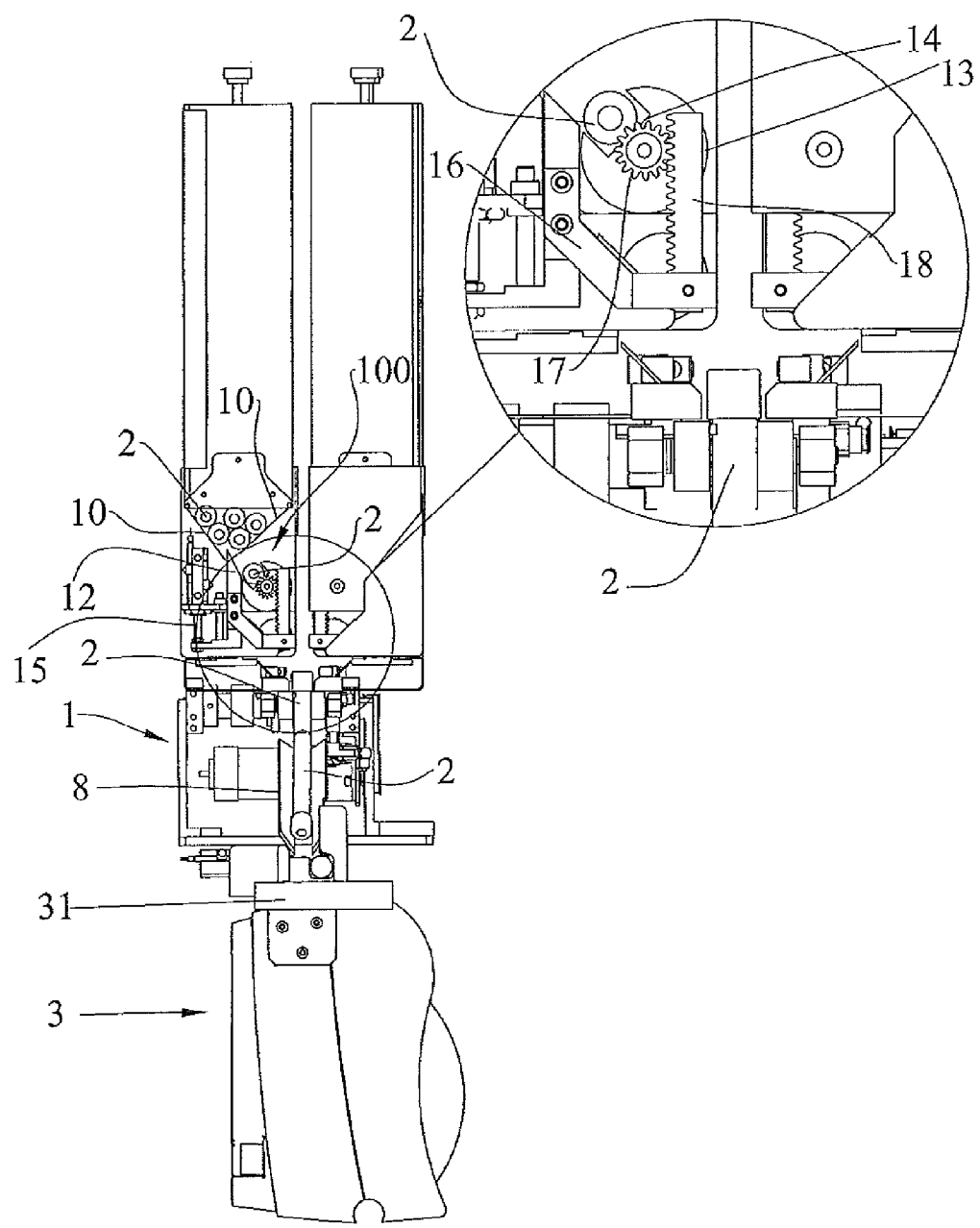
FIG. 2 shows a front side view of the configuration of FIG. 1, with a portion on an enlarged scale.

In this stroke-stop point 7 there may be a gate stop that is suitable for managing the fall of test tubes 2 one by one from said stroke-stop point 7 to a slide 8 (FIGS. 1 and 2) through which the test tube reaches, positioning itself correctly, a housing 19 (FIG. 6) comprised in the labeling machine 3.

This housing 19 enables the test tube to be received in a correct position, stopping the fall from the slide owing to the presence of a guard 20.

Figure 6:
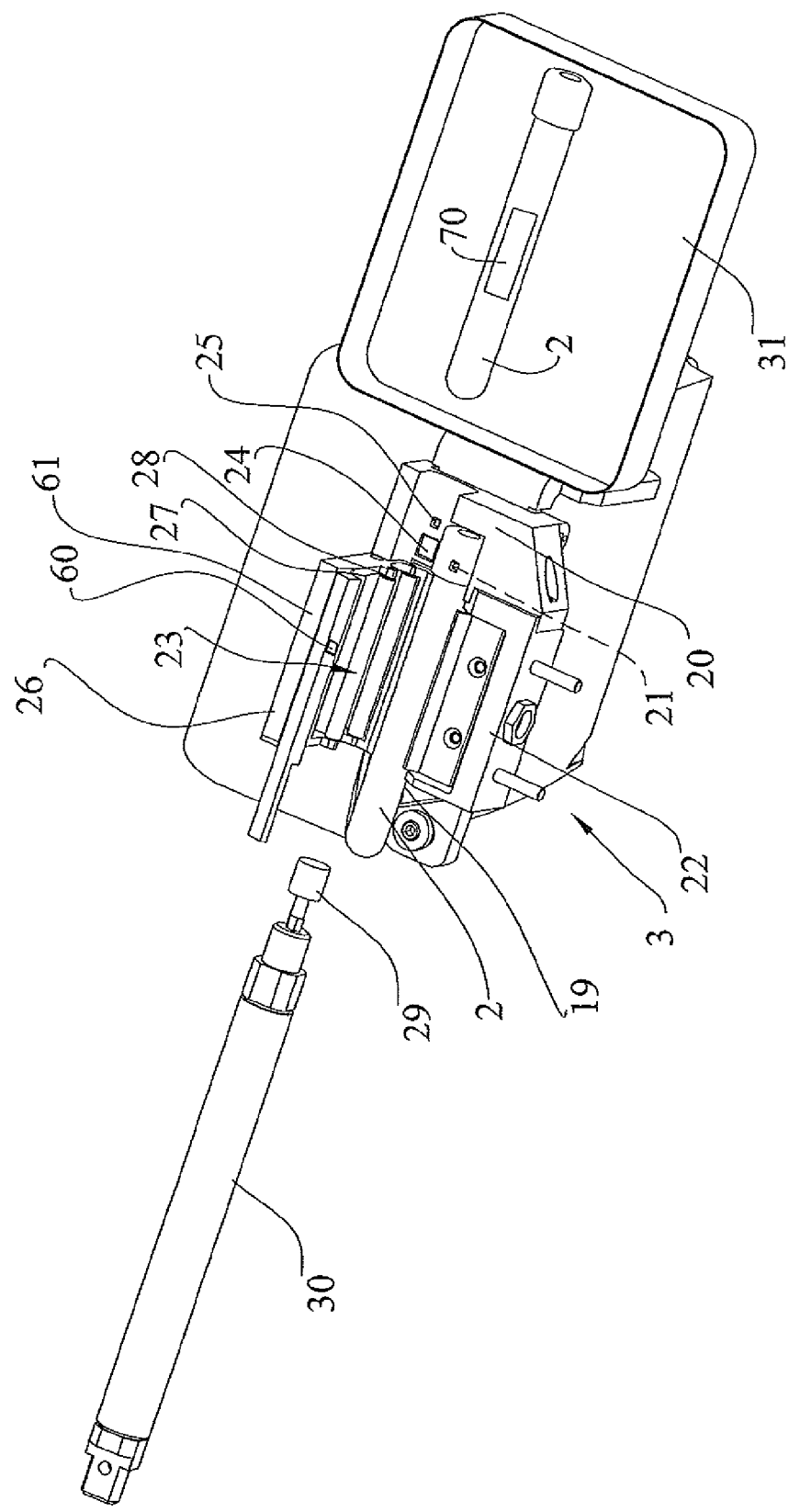
FIG. 6 shows a perspective top view of the automatic labeling machine.

There may be a presence sensor 21, positioned at the base of the housing 19, suitable for reporting the actual arrival of the test tube, enabling a piston 22 to be activated that by becoming activated pushes the test tube to a marking housing 23 (in FIG. 6 the presence sensor 21 is hidden by the test tube 2; the position thereof is however reported).

A second presence sensor 24 and a colour sensor 25 are present in the marking housing 23 so as to make further checks of the test tube, ascertaining the arrival of the test tube and the correctness of the colour of the expected cap and initiating the marking process.

This automatic marking process provides for a printer 26, having received the due information from the control unit 4 on the data to be printed on the adhesive label, producing said label, releasing the label through a slit 27.

The commercially available test tubes already have a label applied to the side body of the test tube, showing the commercial name of the test tube and possibly some information on the dimensions and the type of biological material that they are suitable for containing.

The object of the automatic marking device is to apply the produced adhesive label 70 showing the required information to the side body of the test tube positioned in the marking housing 23, superimposing such label on the label that is already present on the test tube.

For this purpose a label presence sensor 60 is provided that is functionally equivalent to the two previously mentioned presence sensors 21 and 24, which is suitable for identifying the area occupied by the pre-existing label. The label presence sensor in the proposed embodiment is mounted on a support 61 so as to scan the test tube from above but it could also be positioned at the base of the marking housing 23, near the presence sensor 24 and cap-colour sensor 25.

When the test tube 2 has reached the marking housing 23 it is rotated on the axis by a pair of rollers 28, thus enabling the label presence sensor 60 to scan the side wall of the test tube and to identify the initial point of the label and the area occupied thereby.

Once the position of the label on the test tube has been identified the rollers 28 interrupt the rotation, stopping the test tube in a position that is such that at the moment in which the produced label is passed through the slit 27 the produced label can adhere to the test tube by being superimposed on the pre-existing label.

The operation terminates after the test tube has performed a set number of rotations on itself that are generated by the rotation of the pair of rollers 28 that are such that the produced label can be deemed to adhere securely to the test tube.

The rollers 28 could be two "passive" rollers, i.e. could in turn be rotated by a main roller positioned behind the support 61 and moved by an electric motor.

The rotation of the main roller could engage the two rollers, rotating the two rollers in turn.

At the moment in which the rollers 28 interrupt the rotation, a pusher 29 driven by a cylinder 30 (FIG. 6) pushes the test tube from the marking housing 23 inside a tray 31 at the end of the operation, where the labeled test tube can be removed manually.

The invention claimed is:

1. An apparatus for automatically marking laboratory test tubes during the drawing stage of biological material to be analyzed, comprising:
    a plurality of vertical disposed distributors containing different types of test tubes, each distributor selecting and feeding the test tubes to a positioning device for positioning the test tubes relative to a computerized labelling machine comprised in said apparatus and containing a bar code printed on labels, each distributor comprising an automatic device for drawing and discharging a single test tube at a time from a container of test tubes of a selected distributor to said positioning device;
    wherein said container has two pivotally mounted doors disposed at the base of the container, as a lower opening, said test tubes being in substantial disorder inside the container, said automatic device comprising a wedge provided with an oblique surface which performs a vertical movement from bottom to top and vice versa between said two pivotally mounted doors disposed at the base of the container, said wedge entering into the container from the bottom through the lower opening of the container, said wedge remixing the test tubes, said wedge unjamming one of said test tubes, said wedge receiving said one test tube, said one test tube falling from said lower opening into a single housing of a rotor, said rotor being selectively movable according to the vertical position of the wedge, by a vertical rack, integral with the wedge and driving the rotor through a gear between a drawing position of the test tube, in which the wedge is in an upward position, and a discharging position of the test tube, in the positioning device, when the wedge is in a downward position, said oblique surface of the wedge being oblique with respect to the direction of said vertical movement, such that the top end of the wedge can be inserted between two test tubes into the container when the wedge is in the upward position, and said positioning device comprising conveyor belts straightening and moving a plurality of test tubes in the vertical position with a cap facing upwards directly fed by said distributors to said conveyor belts, to a stroke-stop point for managing the fall of test tubes one by one to a slide through which the test tube reaches a housing in the labelling machine in a correct position.

2. The apparatus according to claim 1, wherein the labelling machine comprises:

a guard stopping each test tube falling from said slide;

a presence sensor, positioned at the base of the housing, for reporting the arrival of the test tube, enabling a piston to be activated to push the test tube to a marking housing;

a second presence sensor and a color sensor in the marking housing to make further checks of the test tube, ascertaining the arrival of the test tube and correctness of the color of the cap and initiating the marking process;

a printer, receiving due information from a control unit on the data to be printed on the adhesive label, producing said label, and releasing the label through a slit;

a third presence sensor for identifying the area occupied by the label, mounted on a support so as to scan the test tube; and a pair of rollers for rotating the test tube on an axis, thus enabling the third presence sensor to scan a side wall of the test tube and to identify an initial point of a pre-existing label and the area occupied thereby, and once the position of the label on the test tube has been identified, the rollers interrupt the rotation, stopping the test tube in a position so that at the moment in which the label is passed through said slit and can adhere to the test tube by being superimposed on the pre-existing label, the operation terminates after the test tube has performed a set number of rotations on itself that are generated by the rotation of the pair of rollers so that the produced label can be deemed to adhere securely to the test tube.

* * * * *